(12) United States Patent
Fu

(10) Patent No.: US 7,901,632 B2
(45) Date of Patent: Mar. 8, 2011

(54) ULTRASENSITIVE OLFACTORY SYSTEM FABRICATION WITH DOPED AEROGELS

(76) Inventor: Chi Yung Fu, San Francisco, CA (US)

( * ) Notice: Subject to any disclaimer, the term of this patent is extended or adjusted under 35 U.S.C. 154(b) by 0 days.

(21) Appl. No.: 11/281,048

(22) Filed: Nov. 16, 2005

(65) Prior Publication Data

US 2006/0104864 A1    May 18, 2006

Related U.S. Application Data

(60) Provisional application No. 60/628,698, filed on Nov. 16, 2004.

(51) Int. Cl.
*G01N 7/00* (2006.01)
(52) U.S. Cl. .............. 422/83; 422/68.1; 422/84; 422/90; 422/98; 436/151; 436/181; 73/23.3; 73/23.4
(58) Field of Classification Search .................. 422/55, 422/68.1, 82.05, 82.06, 82.07, 82.08, 82.09, 422/83, 84, 98; 436/164, 165, 172, 151, 436/181; 73/23.3, 23.4, 23.34
See application file for complete search history.

(56) References Cited

U.S. PATENT DOCUMENTS

| | | | |
|---|---|---|---|
| 5,489,988 A * | 2/1996 | Ackley et al. ................. | 356/436 |
| 5,589,396 A * | 12/1996 | Frye et al. ........................ | 436/73 |
| 5,637,507 A * | 6/1997 | Wicks et al. .................. | 436/166 |
| 5,650,311 A * | 7/1997 | Avnir et al. .................... | 435/176 |
| 5,786,219 A * | 7/1998 | Zhang et al. ................... | 436/523 |
| 5,922,537 A * | 7/1999 | Ewart et al. ........................ | 435/6 |
| 5,994,150 A * | 11/1999 | Challener et al. .............. | 436/518 |
| 6,057,377 A * | 5/2000 | Sasaki et al. ..................... | 521/99 |
| 6,078,705 A * | 6/2000 | Neuschafer et al. ............ | 385/12 |
| 6,251,342 B1 * | 6/2001 | Narula et al. .............. | 422/82.07 |
| 6,319,674 B1 * | 11/2001 | Fulcrand et al. ................ | 435/7.1 |
| 6,331,438 B1 * | 12/2001 | Aylott et al. ..................... | 436/172 |
| 6,368,558 B1 * | 4/2002 | Suslick et al. .................... | 422/55 |
| 6,485,987 B1 * | 11/2002 | Charych et al. ............... | 436/535 |
| 6,495,102 B1 * | 12/2002 | Suslick et al. .................... | 422/55 |
| 6,537,829 B1 * | 3/2003 | Zarling et al. ................. | 436/514 |
| 6,598,459 B1 * | 7/2003 | Fu ................................. | 73/23.34 |
| 6,610,482 B1 * | 8/2003 | Fodor et al. ......................... | 435/6 |
| 6,686,150 B1 * | 2/2004 | Blackburn et al. ................. | 435/6 |

* cited by examiner

*Primary Examiner* — Jill Warden
*Assistant Examiner* — Dwayne K Handy

(57) ABSTRACT

An array of sensor elements is formed by the incorporation of sensing materials into porous structures, creating sensing systems with extremely large surface areas with sensing molecules attached to mimic the large number of cilia of an olfactory system. In each sensor element, the sensing material or molecules are attached to spacer molecules or groups, which are attached to linker molecules or groups, which are attached to the porous substrate material. More specifically, a porphyrin doped aerogel material is used. The porphyrin sensing material is attached to the aerogel throughout its high surface area pore space. The porphyrin is covalently bonded to the silica network of the aerogel with a triethoxysilyl group linker that covalently attaches to the aerogel, and an alkyl group spacer.

13 Claims, 3 Drawing Sheets

ULTRASENSITIVE OLFACTORY SYSTEM FABRICATION WITH DOPED AEROGELS

RELATED APPLICATIONS

This application claims priority from provisional application 60/628,698 filed Nov. 16, 2004.

BACKGROUND OF THE INVENTION

This invention relates generally to ultrasensitive sensors, including sensors that may be used individually or that may be used in an array in artificial olfactory systems, and more particularly to the attachment of sensing materials to substrates, most particularly porphyrin sensing materials to aerogel substrates, in ultrasensitive sensors.

The human olfactory system has about 100 million olfactory cells and each cell has about 10 cilia resulting in about 1 billion sensing elements. The olfactory system of canines has orders of magnitude more sensing elements. It is this enormous number of sensing elements that gives the ultrasensitivity to biological olfactory systems. While the number of olfactory sensors is very large, the number of different olfactory sensors is much smaller, about 1000 in a human. Identification of an odor is through pattern recognition and neural processing.

Artificial olfactory systems attempt to model the biological olfactory system. Arrays of nonspecific chemical sensors are used with signal processing to identify odorants through pattern recognition. Artificial olfactory systems are presently limited by the sensitivity of the sensors and the processing techniques.

U.S. Pat. No. 6,598,459 to Chi Yung Fu describes an approach to an ultrasensitive sensor element and array for an artificial olfactory system. Ultrasensitivity is obtained by producing a very large surface area on the sensor to mimic the very large number of sensing elements in the biological system. Also sophisticated fuzzy logic and neural network processing are used to identify the detected patterns. The sensor is formed with a substrate of a very high surface area material (a "surface area increasing material") on a conventional sensor body, typically an acoustic device or resonator such as a quartz crystal microbalance (QCM), a surface acoustic wave device (SAW), or a micromachined resonator. The high surface area material is preferably an aerogel (or xerogel), but may also include nanotubes, porous carbons, or micromachined materials. The high surface area material is coated with an odorant attracting or detecting material (sensing material), typically a polymer, to which the target molecules attach.

One particular combination of interest is porphyrin coated aerogel. There are a number of known techniques to deposit porphyrins onto substrates, including casting, Langmuir-Blodgett (LB) techniques, and self-assembly deposition. The casting method dissolves an appropriate porphyrin into chloroform and then applies the solution onto the substrate. Once the chloroform evaporates, a thin film of porphyrin will be left behind on the surface of the substrate. However, there is concern for repeatability and uniformity using such an approach to deposit porphyrins into porous structures such as aerogel. The LB techniques are only good for deposition on another layer and not good for filling the pores of a structure. Self-assembly seems appropriate but there are concerns regarding the penetration of the porphyrin into the porous structure of aerogel and furthermore the manufacturing cost and complexity will be high.

Thus it is important to obtain sensors in which the sensing material is strongly attached to the porous substrate material. Otherwise the benefit of the high surface area of the substrate will be lost.

SUMMARY OF THE INVENTION

The invention is an array of sensor elements that are formed by the incorporation of sensing materials into porous structures, creating sensing systems with extremely large surface areas with sensing molecules attached to mimic the large number of cilia of an olfactory system. In each sensor element, the sensing material or molecules are attached to spacer molecules or groups, which are attached to linker molecules or groups, which are attached to the porous substrate material. This arrangement provides for strong attachment of the sensing material to the substrate. The invention also allows the creation of ultrasensitive single sensors.

The porous structure with sensing material forms a part of a conventional sensor, e.g. QCM, SAW device, resonator, or optical sensor. An array of such sensors combined with a measurement device and a signal processor form an artificial olfactory system. In an artificial olfactory system, each sensor is made of a different sensing material, but the different sensing materials are typically related, i.e. they are different species from a single family, e.g. porphyrins. The different sensing materials are nonspecific and together provide a signature that identifies target species. But the linkers and spacers in all the sensors of the array are the same, which greatly facilitates fabrication.

More specifically, a porphyrin doped aerogel material is used. The aerogel provides the high surface area porous structure. The porphyrin is the sensing material and is attached to the aerogel throughout its high surface area pore space. The porphyrin doped aerogel is made using the solution sol-gel process. The intact porphyrin is covalently bonded to the silica network of the aerogel through a spacer with a linker or bridge. More specifically, the linker or bridge is a terminal triethoxysilyl group that covalently attaches to the aerogel, and the spacer is an alkyl group.

DETAILED DESCRIPTION OF THE INVENTION

Figure 1:
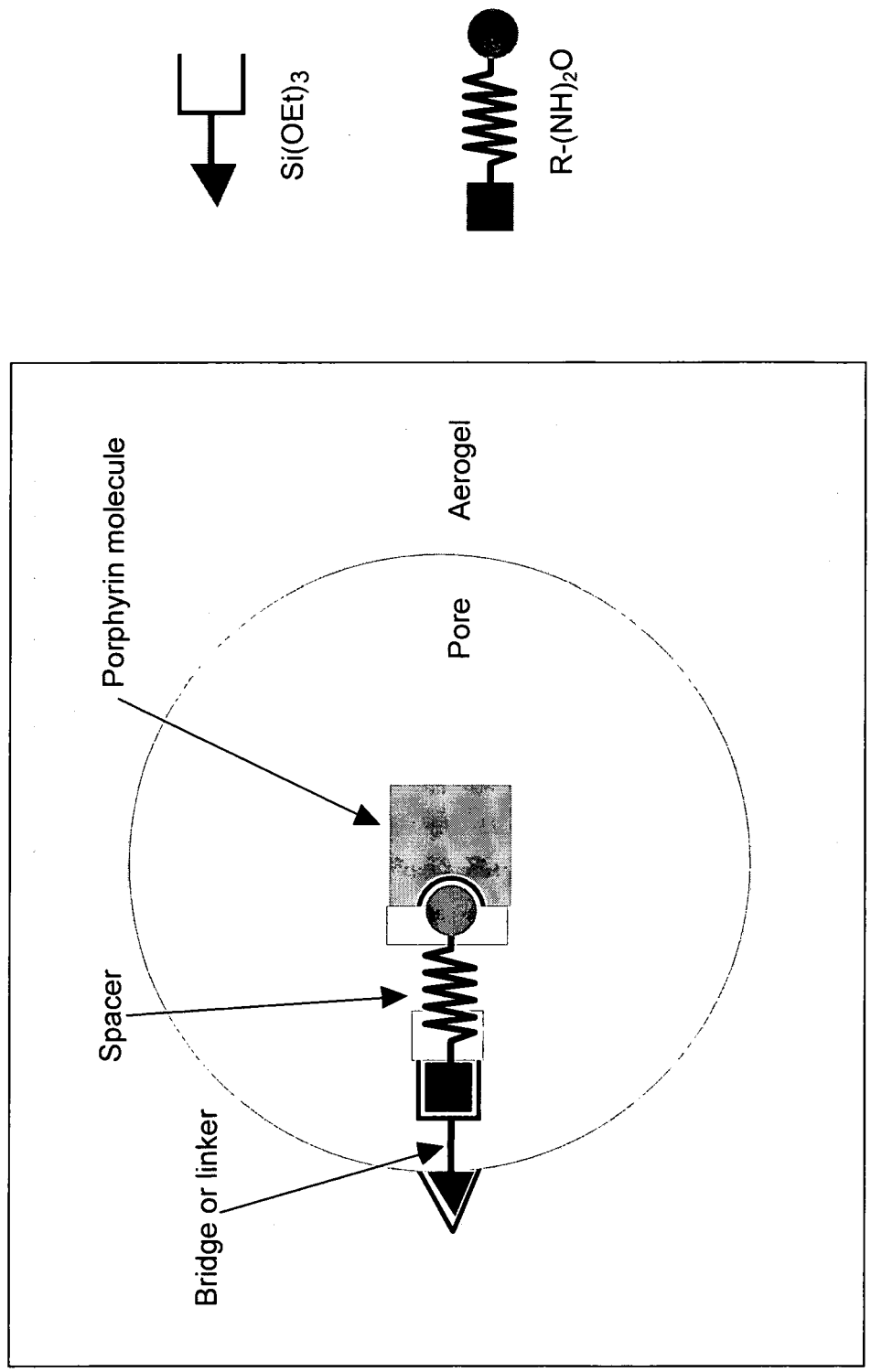
FIG. 1 illustrates the attachment of a sensing molecule in the pore of an aerogel substrate through a bridge or linker molecule and a spacer molecule.
Figure 2A:
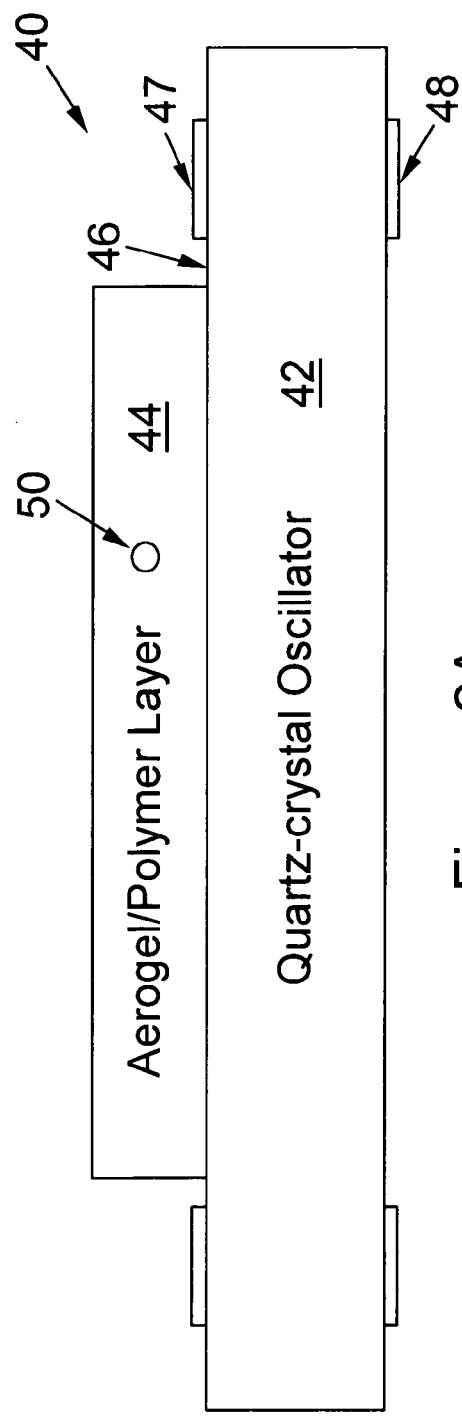
FIG. 2A is a cross sectional view of a sensor having a layer of aerogel, with a polymer coating, on top of a piezoelectric crystal.
Figure 2B:
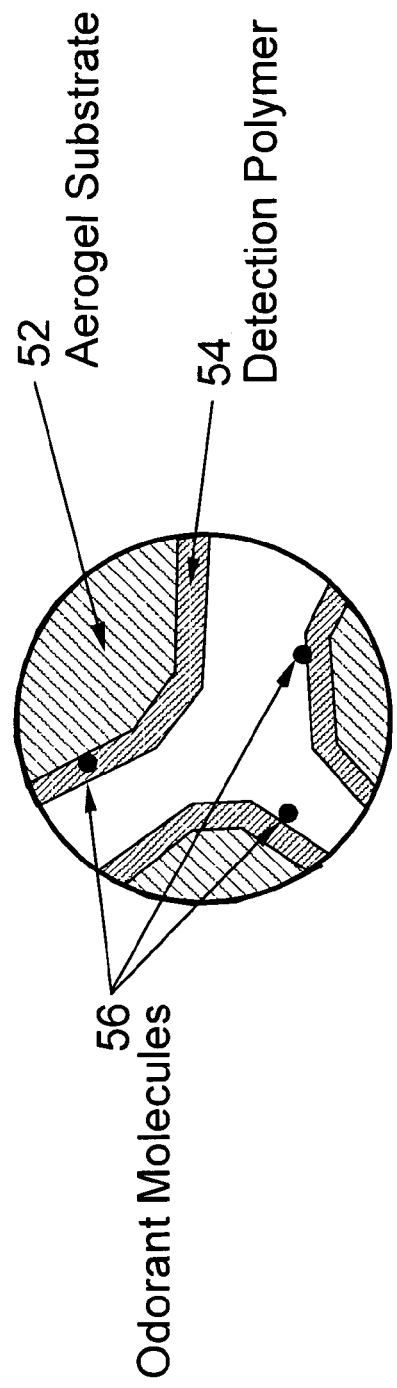
FIG. 2B shows a magnified area of the aerogel/polymer layer of FIG. 2A.
Figure 3:
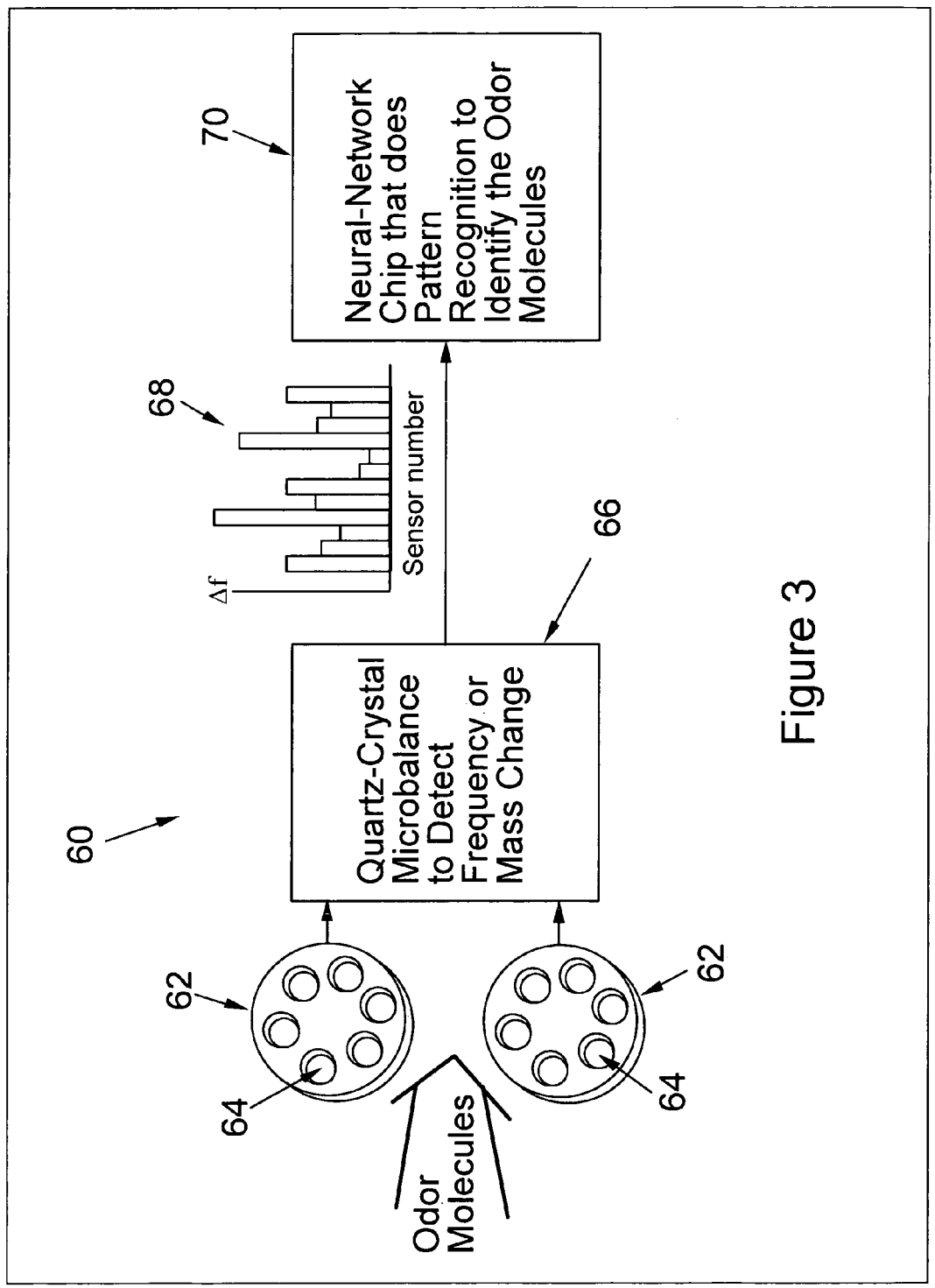
FIG. 3 shows a complete artificial olfactory system with two sensing units, a measurement unit, and a neural network or intelligent processing system.

The basic principles of an ultrasensitive sensor element and array are described in U.S. Pat. No. 6,598,459, which is herein incorporated by reference. However the type of sensor is not limited to the types of sensors shown therein, but more broadly applies to any other type of sensor where a high surface area may provide a higher amount of sensing material, e.g. optical sensors.

In this invention, materials such as aerogel, xerogel, nanotubes, porous carbon, zeolites, man-made structures such as those created by micromachining or nanotube-like or dendrite-like growth processes, and any other materials that can provide large surface areas relative to the physical dimensions of the sensor, are used as a substrate for the sensing system. Two appropriate molecules, A and B, are chosen to link the sensing molecule, S, to the substrate, Su. While the following description is in terms of single molecules, there are of course many similar molecules attached through many spacer-linkers to each sensor to provide the high sensitivity.

Molecule A has the attribute of having one side chain that can easily attach to the surface of the substrate. Another end of molecule A has the property to attach easily to the B molecule. Molecule A is called a linker or bridge. Molecule B has the attribute of having a side chain that can attach to molecule A, whereas another end can attach to the sensing molecule. Molecule B also has two additional attributes. It acts as a space extender so that the attached sensing molecule S would as much as possible be located in the center of the voids or pores of the porous substrate. Secondly, molecule B also acts as a "spring" or a spacer to release stress and tension to make the sensing system more reliable. Molecule B is called a spacer.

The sensing molecules can be chemically based for chemical detection as well as biologically based for biological sensing. Examples of sensing molecules can be different types of porphyrin molecules or different types of amino acids. The members within these two families of molecules are structurally similar but have diverse chemical and biologically different properties obtained simply by changing one or a few atoms within the molecular structure. The similarity of the structures within the same family means that once an appropriate molecule B is found, then molecule B can be the spacer molecule for every member of the same family, and thus it can attach to the same A molecule to link to the substrate. This allows very efficient development of a sensor array such as an olfactory system. There may be circumstances that molecule A and molecule B can be collapsed into one single molecule. In other words, it acts as both the linker and the spacer, i.e. one end attaches directly to S and another end attaches directly to Su while providing both functions of the linker and the spacer.

Another aspect of this invention is that molecules A, B, and S can be "pre-fabricated together" in a chemical synthesis house and these "macromolecules" will be incorporated into the porous structures as in the case of doping in semiconductor. This doping process allows a divide-and-conquer approach that makes implementing different ultra-sensitive sensors relatively simple and cost effective. Such an approach represents essentially a single-step process and thus is elegantly simple. Doping in semiconductors has been done routinely in integrated circuit processing and is a highly manufacturable process.

The above invention can be used for implementing a sensing system using different porphyrin molecules into xerogel/aerogel structures to form a sensing array. The sensing array utilizes known types of sensors but their sensitivity is greatly enhanced by the high surface area with attached sensing material. The sensor array can be used, with appropriate signal processing, e.g. fuzzy logic and neural networks, in an artificial olfactory system or electronic nose. A single high sensitivity sensor may also be used by itself for various applications.

FIG. 1 schematically shows a Mn(III) porphyrin molecule attached to a functionalized alkoxide linker —$Si(OEt)_3$ (triethoxysylil) through a spacer. The linker attaches to the aerogel substrate. The linkage forms a bridge between the porphyrin molecule and the aerogel matrix. By using the same linker, from the perspective of the aerogel/xerogel, it does not matter what porphyrin is attached. In other words, once successfully developed for one porphyrin, the technology is essentially applicable to all other porphyrins. This drastically reduces the time of development of the sensor array. FIG. 1 also shows an alkyl spacer between the porphyrin molecule and the linker. The spacer decreases the mechanical tensions during the drying process and thus would increase yield and reliability.

The viability of such an approach to prepare such doped aerogels has already been shown in the field of catalysis. M. Bonnett et al., "A New Mesoporous Hybrid Material: Porphyrin-Doped Aerogel as a Catalyst for the Epoxidation of Olefins," Adv. Funct. Mater. 2002, 12, No. 1, January, 39-42, shows the synthesis of Mn(III) porphyrin and porphyrin doped aerogel. L. Schmid et al., "A mesoporous ruthenium silica hybrid aerogel with outstanding catalytic properties in the synthesis of N,N-diethylformamide from CO2, H2 and diethylamine," Chem. Commun., 1999, 2302-2304, shows a ruthenium phosphine complex functionalized by silyl ether groups immobilized within a silica matrix to form doped aerogel or xerogel. Similar fabrication techniques have also been used to prepare optical materials for second harmonic generation experiments. J. P. Boilot et al., "Covalent Grafting of Optically Active molecules on Silica Gels," shows the grafting of active organic molecules onto a xerogel silica matrix using functionalized alkoxides with an alkyl spacer to limit the degrees of freedom of the molecules. These papers are herein incorporated by reference. Thus the present invention uses similar materials produced in other fields for a totally new use, to make ultrasensitive sensors.

As shown in FIG. 2A, a sensor element 40 is formed from a piezoelectric (PZ) crystal oscillator 42 having an aerogel/polymer layer 44 on a surface 46. A pair of electrodes 47, 48 on opposed surfaces of PZ crystal 42 are used to apply a voltage across the crystal to induce oscillation. Layer 44 provides a high surface area and the ability to capture odorant molecules. A region 50 is shown in greater detail in FIG. 2B. Aerogel substrate 52 has a thin coating of detection polymer 54 thereon. Odorant molecules 56 penetrate the void spaces 58 in the aerogel substrate 52. Changes in the resonant frequency of oscillator 42 produced by different odorant molecules are detected. The doped aerogel of the present invention, as illustrated in FIG. 1, is used to form the layer 44. Crystal 42 is generally representative of any type of sensor on which layer 44 could be effective, e.g. an optical sensor such as a waveguide.

As shown in FIG. 3, artificial olfactory system 60 has a pair of sensor units 62, each of which contains a plurality (e.g. 6) of sensor elements 64. The outputs of the sensor elements 64 are measured by measurement device 66. Device 66 is a frequency measurement unit, e.g. a quartz crystal microbalance, to detect frequency or mass change. Measurement device 66 produces a signature 68 which is input into an intelligent signal processor 70, e.g. a neural network, that performs pattern recognition to detect, recognize and identify the odor molecules. The individual sensor elements 64 are nonspecific, i.e. they all respond to each target molecule, producing a signature for that target, but different signatures for different targets. Thus the individual sensors can be made with different materials from a particular family, e.g. porphyrins, and the invention provides a single way to attach all the different sensing materials.

Changes and modifications in the specifically described embodiments can be carried out without departing from the scope of the invention which is intended to be limited only by the scope of the appended claims.

I claim:

1. A sensor array for an artificial olfactory system for detecting various targets, comprising:
- a plurality of sensor elements, each sensor element comprising:
- a sensor body;
- a high surface area substrate on the sensor body and having a porous structure, the surface area of the substrate being substantially greater than the physical dimensions of the sensor body;
- linker molecules attached to the substrate throughout its porous structure;
- spacer molecules attached to the linker molecules;
- sensing molecules attached to the spacer molecules throughout the porous structure of the substrate;
- each sensor element being non-specific to the targets and responding non-specifically to many different targets, the array of sensor elements producing signatures for various targets;
- wherein all sensor elements are formed of the same substrate, linker molecules and spacer molecules, and each sensor element is formed of a different sensing molecule selected from a related family of sensing molecules;
- wherein the substrate is an aerogel or xerogel, the sensing molecule is a porphyrin, the linker molecule is a triethoxysylil, and the spacer molecule is an alkyl.

2. An artificial olfactory system for detecting various targets, comprising:
- a sensor array comprising a plurality of sensor elements, each sensor element comprising:
- a sensor body;
- a high surface area substrate on the sensor body and having a porous structure, the surface area of the substrate being substantially greater than the physical dimensions of the sensor body;
- linker molecules attached to the substrate throughout its porous structure;
- spacer molecules attached to the linker molecules;
- sensing molecules attached to the spacer molecules throughout the porous structure of the substrate;
- each sensor element being non-specific to the targets and responding non-specifically to many different targets, the array of sensor elements producing signatures for various targets;
- wherein all sensor elements are formed of the same substrate, linker molecules and spacer molecules, and each sensor element is formed of a different sensing molecule selected from a related family of sensing molecules;
- a measurement device connected to the sensor array to measure the outputs of the sensor elements of the sensor array;
- a pattern recognizing intelligent signal processor connected to the measurement device and trained to detect a target by pattern recognition of the composite responses of all the sensor elements of the sensor array;
- wherein the substrate is selected from aerogel, xerogel, nanotubes, porous carbon, zeolites, or structures created by micromachining or nanotube- or dendrite-growth processes.

3. The artificial olfactory system of claim 2 wherein the sensor bodies are piezoelectric crystal oscillators, the measurement device is a frequency measuring device for measuring changes in resonant frequency of the crystal oscillators caused by changes in mass of the sensor body substrates from binding of target molecules to sensing molecules, and the signal processor is a neural network.

4. The artificial olfactory system of claim 2 wherein the sensing molecules are a porphyrin or an amino acid.

5. The artificial olfactory system of claim 2 wherein the linker molecule is a triethoxysylil, and the spacer molecule is an alkyl.

6. A method of forming a sensor array for an artificial olfactory system for detecting various targets, comprising:
- forming a plurality of sensor elements, each sensor element comprising a sensor body, a high surface area substrate on the sensor body and having a porous structure, the surface area of the substrate being substantially greater than the physical dimensions of the sensor body, linker molecules attached to the substrate throughout its porous structure, spacer molecules attached to the linker molecules, and sensing molecules attached to the spacer molecules throughout the porous structure of the substrate, each sensor element being non-specific to the targets and responding non-specifically to many different targets, the array of sensor elements producing signatures for various targets;
- wherein all sensor elements are formed of the same substrate, linker molecules and spacer molecules, and each sensor element is formed of a different sensing molecule selected from a related family of sensing molecules;
- wherein the substrate is an aerogel or xerogel, the sensing molecule is a porphyrin, the linker molecule is a triethoxysylil, and the spacer molecule is an alkyl.

7. The method of claim 6 wherein the linker, spacer, and sensing molecules are prefabricated into linker-spacer-sensing macromolecules and the macromolecules are incorporated into the porous structure of each substrate by a doping process.

8. The artificial olfactory system of claim 2 wherein the sensing molecule is a porphyrin.

9. The artificial olfactory system of claim 2 wherein the sensing molecule is an amino acid.

10. The artificial olfactory system of claim 2 wherein the linker molecule is a triethoxysylil.

11. The artificial olfactory system of claim 2 wherein the spacer molecule is an alkyl.

12. The artificial olfactory system of claim 2 wherein the substrate is an aerogel or xerogel, the sensing molecule is a porphyrin, the linker molecule is a triethoxysylil, and the spacer molecule is an alkyl.

13. The sensor array of claim 1 wherein the sensor bodies are piezoelectric crystal oscillators.

* * * * *